United States Patent
Falsafi et al.

(10) Patent No.: US 6,818,682 B2
(45) Date of Patent: Nov. 16, 2004

(54) MULTI-PART DENTAL COMPOSITIONS AND KITS

(76) Inventors: Afshin Falsafi, P.O. Box 33427, St. Paul, MN (US) 55133-3427; Mark S. Konings, P.O. Box 33427, St. Paul, MN (US) 55133-3427; Joel D. Oxman, P.O. Box 33427, St. Paul, MN (US) 55133-3427; Richard P. Rusin, P.O. Box 33427, St. Paul, MN (US) 55133-3427; Edward J. Winters, P.O. Box. 33427, St. Paul, MN (US) 55133-3427

(*) Notice: Subject to any disclaimer, the term of this patent is extended or adjusted under 35 U.S.C. 154(b) by 454 days.

(21) Appl. No.: 09/838,950

(22) Filed: Apr. 20, 2001

(65) Prior Publication Data

US 2003/0018098 A1 Jan. 23, 2003

(51) Int. Cl.$^7$ ............................................. A61K 6/083
(52) U.S. Cl. ...................... 523/116; 522/908; 523/117; 106/35; 433/228.1
(58) Field of Search ................. 523/116, 117; 433/228.1; 106/35; 522/908

(56) References Cited

U.S. PATENT DOCUMENTS

| | | | |
|---|---|---|---|
| 3,655,605 A | 4/1972 | Smith et al. | 523/116 |
| 3,814,717 A | 6/1974 | Wilson et al. | 523/116 |
| 4,143,018 A | 3/1979 | Crisp et al. | 433/228.1 |
| 4,209,434 A | 6/1980 | Wilson et al. | 523/116 |
| 4,288,355 A | 9/1981 | Anderson et al. | 523/116 |
| 4,360,605 A | 11/1982 | Schmitt et al. | 523/116 |
| 4,376,835 A | 3/1983 | Schmitt et al. | 523/116 |
| 4,591,384 A | 5/1986 | Akahane et al. | 433/228.1 |
| 4,695,251 A | 9/1987 | Randklev | 433/8 |
| 4,872,936 A | 10/1989 | Engelbrecht | 523/116 |
| 5,063,257 A * | 11/1991 | Akahane | 523/116 |
| 5,074,916 A | 12/1991 | Hench et al. | 106/35 |
| 5,130,347 A | 7/1992 | Mitra | 433/228.1 |
| 5,154,762 A | 10/1992 | Mitra et al. | 523/116 |
| 5,179,135 A | 1/1993 | Ellis et al. | 523/116 |
| 5,334,625 A | 8/1994 | Ibsen et al. | 523/116 |
| 5,367,002 A * | 11/1994 | Huang et al. | 523/116 |
| 6,136,885 A * | 10/2000 | Rusin et al. | 523/116 |
| 6,214,101 B1 | 4/2001 | Nakaseko | 523/116 |
| 6,217,644 B1 | 4/2001 | Matsunae et al. | 106/35 |
| 6,306,923 B1 * | 10/2001 | Thepot et al. | 526/262 |
| 6,313,192 B1 * | 11/2001 | Anstice et al. | 523/116 |

FOREIGN PATENT DOCUMENTS

| | | | |
|---|---|---|---|
| EP | 0 173 567 A2 | 3/1986 | |
| EP | 0 510 211 A1 | 10/1992 | |
| WO | WO 88/05651 | 8/1988 | |
| WO | WO 93/16675 | 9/1993 | |
| WO | WO 95/22956 | 8/1995 | |
| WO | WO 97/47272 | 12/1997 | A61K/6/083 |
| WO | WO 98/30192 | 7/1998 | A61K/6/083 |
| WO | WO 99/03444 | 1/1999 | A61K/6/083 |

OTHER PUBLICATIONS

Robert G. Craig, *Restorative Dental Materials*, 9$^{th}$ edition (1993), p. 197.
U.S. Ser. application No. 09/753,945, filed Jan. 3, 2001.

\* cited by examiner

*Primary Examiner*—Peter Szekely

(57) ABSTRACT

The inventive dental composition comprises (a) a part A comprising at least one polyacid and at least one polymerizable component; and (b) a part B comprising water, wherein the composition further comprises an oxidizing agent, a reducing agent, and reactive fillers in at least one of part A or part B and wherein at least one of the polyacid, oxidizing agent, and reducing agent is in a disperse phase. The dental composition can be used in many dental applications and is particularly suited for use as a cement.

24 Claims, No Drawings

US 6,818,682 B2

MULTI-PART DENTAL COMPOSITIONS AND KITS

TECHNICAL FIELD

The present invention relates to a dental composition that exhibits long-term stability, on the order of greater than 12 months, and can be conveniently formulated as in a paste-paste or paste-liquid system. In one embodiment, the composition contains, among other components, at least one polyacid and at least one redox catalyst. At least one of the polyacid and redox catalyst exist in a disperse phase.

BACKGROUND

In general, a dental composition such as glass ionomer cements comprise ionic polymers and reactive glasses. The mixing of the two components in an aqueous environment initiates a setting reaction. Glass ionomer cements find utility in dental and medical applications, where the cements are used on, e.g., tooth and bone structures. Conventional glass ionomer cements have been supplied as a two-part powder-liquid system, where an ionic polymer (typically polyacrylic acid) is dissolved in water and a reactive glass (typically an acid-reactive glass) is in powder form. See, e.g. Robert G. Craig, *Restorative Dental Materials*, 9$^{th}$ edition (1993) at page 197.

One advancement over the conventional glass ionomer cements is the hybrid ionomer cement, also known as resin modified ionomer cement. It contains, among other components, at least one polymerizable compound and polymerization initiators. The hybrid ionomer cement typically has liquid and powder components. The liquid component can contain an ionic polymer such as polyacrylic acid (the acid may be functionalized with ethylenically unsaturated moieties), a polymerizable compound, water, and optional redox catalysts, which functions as part of the initiating system. The powder component can contain basic-reactive glass and redox catalysts, such as oxidizing and reducing agents.

It has been recognized by those skilled in the art that a powder-liquid system, such as those of conventional or hybrid glass ionomer cement, can present drawbacks. For example, extra skill and time may be required to dispense proportionate amounts of the powder and the liquid and mixing them to form the cement.

To overcome the disadvantages of the powder-liquid system, some skilled in the art have investigated alternative systems. For example, U.S. Pat. No. 6,136,885 (Rusin et al.) discloses a ionomer cement system comprising (a) an organic composition having a liquid ingredient that is free of water, and (b) an aqueous composition having a liquid ingredient comprising water.

In U.S. Pat. No. 5,154,762 (Mitra et al.), a dental cement contains water, acid-reactive filler, water-miscible acidic polymer, ethylenically-unsaturated moiety, photoinitiator, water-soluble reducing agent, and water-soluble oxidizing agent. Two part paste-paste cements were disclosed at column 2, lines 58 to 66.

While the foregoing dental compositions may have been us compositions are sought.

SUMMARY

In brief summary, in one embodiment, the present invention provides a dental composition comprising (a) a part A comprising at least one polyacid and at least one polymerizable component and (b) a part B comprising water. The composition further comprises an oxidizing agent, a reducing agent (both being part of a redox catalyst system), and reactive fillers in at least one of part A or part B. One uniqueness of the present invention is that at least one of the following components exist in a disperse phase: the polyacid, the oxidizing agent, and the reducing agent.

In use, when parts A and B are mixed together to form the inventive composition, the reactive filler, the polyacid, and the oxidizing agent become chemically reactive. Upon mixing, parts A and B are at least partially miscible with one another. Parts A and B can be supplied in paste-paste form or paste-liquid form.

The inventive composition has shelf stability on the order of months, typically at least 12 months. The inventors have discovered that such long-term stability can be achieved when at least one of the following components is in the disperse phase: the polyacid and the redox catalyst.

The term "disperse phase" means generally a two-phase system where one phase contains discrete particles distributed throughout a bulk substance, the particles being the disperse phase, and the bulk substance being the continuous phase. In one inventive embodiment, the continuous phase is the polymerizable component and at least a portion of the polyacid and/or redox catalyst exists as the discrete particles. By "disperse phase," it is also meant that not necessarily the entire polyacid and/or redox catalyst need to be insoluble in the polymerizable component. Some of the polyacid and/or redox catalyst can be soluble therein. The dispersed particles are generally less than about 60 micrometers in average diameter.

One skilled in the art can determine whether the polyacid and/or the redox catalysts exist in a disperse phase by using any number of separation techniques, such as centrifugation or filtration. In these techniques, if there is a disperse phase, it will phase separate out of the bulk substance, either catching on the filter paper in the case of filtration or phase separate and settle out in the case of centrifugation. The separation test method should be performed when the polyacid and/or redox catalyst is the presence of a polymerizable component. That is, the other components of the inventive dental composition, such as the filler, should not be part of the system during testing to determine the presence of a disperse phase.

Although numerous references have disclosed the use of polyacid and redox catalyst in ionomer cement compositions, the inventors are not aware of any reference that disclose or suggest using either one in a disperse phase. The inventors have been able to formulate resin modified ionomer cement compositions having stability exceeding 12 months.

The inventors have further discovered an alternative approach to achieving long-term stability in the dental composition. This approach uses a particular monoacid that is dissolved in the polymerizable component. The monoacid, as the name implies, contains acid functionality, but does not contain hydroxyl functionality, particularly primary or secondary hydroxyl groups. When using this approach it is not necessary to have the polyacid or the redox catalyst in a disperse phase.

Instabilities may exist in conventional and resin modified ionomer cement systems. For example, in some systems, peroxide oxidizing agents can react with compounds having acid functionality when both are solubilized, i.e., dissolved in some carrier, such as water, hydroxylic solvents, or short chain hydroxylic monomers all of which are widely used in glass ionomer cements. Oxidizing agents and reducing agents can react in the presence of water and initiate the setting of the polymerizable component unless the agents are first encapsulated. The polyacid can react with reactive fillers, especially with fluoroaluminosilicate (FAS) glass in the presence of water. The polyacid can react many reducing agents, such as amines and/or sulfinates, to induce premature free radical polymerization. Thus, the inventors have devised a unique solution to the instabilities that may be present in a dental composition by deliberately putting the polyacid and/or the redox catalyst in a disperse phase or by using a particular type of monoacid dissolved in the polymerizable component.

The inventive dental composition can be used in various applications, such as dental adhesives, artificial crowns, anterior or posterior fillings, casting materials, cavity liners, cements, coating compositions, mill blanks, adhesives and cements for affixing orthodontic brackets and appliances, endodontic cements, restoratives, prostheses, and sealants. The composition is especially suited for use as a cement. The composition can be placed in the mouth and cured in situ. Alternatively, it can be fabricated in a prosthesis outside the mouth and subsequently adhered in place in the mouth.

DETAILED DESCRIPTION OF THE INVENTION

The inventive dental composition can be formulated as a one- or a two-components system. The two-component system is preferred. One suitable two-component system comprises (a) a part A comprising at least one polyacid compound, at least one polymerizable component, and at least one oxidizing agent; and (b) a part B comprising water, reactive fillers, and at least one reducing agent. In such a two-component system, at least one of the polyacid compound, oxidizing agent, and reducing agent is dispersed in the polymerizable component. The composition comprises about 5 to 35 parts water, based on the total weight of the composition. Each component is discussed below in detail.

Polyacid

The polyacid preferably resides in part A. Useful polyacids are polymers having sufficient pendent ionic groups to undergo a setting reaction in the presence of reactive fillers and water. The polyacid may or may not contain polymerizable groups to enable the resulting composition to be cured when exposed to redox and/or photoactivated polymerization initiators. The polyacid should be partially or fully insoluble in the polymerizable component. The polyacid constitutes at most about 50 parts, preferably about 5 to 25 parts of the total composition.

Examples of suitable polyacid compounds include polymers derived from the following acid: acrylic acid, methacrylic acid, itaconic acid, maleic acid, glutaconic acid, aconitic acid, citraconic acid, mesaconic acid, fumaric acid, tiglic acid, and combinations thereof. Preferred polyacids are described in U.S. Pat. No. 5,130,347 (Mitra). A particularly preferred polyacid is described in Example 11 of U.S. Pat. No. 5,130,347 and when used, this polyacid constitutes at most about 30, preferably about 5 to 25 parts by weight of the total composition.

Polymerizable Component

The polymerizable component resides in part A and/or part B. The inventive cement contains about 5 to 75, preferably about 10 to 50, more preferably about 15 to 45 parts by weight of the polymerizable component, based on the total weight of the composition. Useful polymerizable components are monomers, oligomers, or polymers containing a polymerizable group selected from the following: free radically polymerizable groups, cationically polymerizable groups, or mixtures thereof. It is within the scope of this invention that a polyacid functions as a polymerizable component. The polymerizable component is incapable of fully dissolving the polyacid or the redox catalyst, although partial solubility is possible. The polymerizable component is partially or fully water soluble, meaning that the component is soluble in water at concentrations of at least 3% by weight.

The polymerizable component has a molecular weight between about 100 to 5000, and preferably, between about 200 and 1000. Mixtures of both higher and lower molecular weight materials are also contemplated as providing special benefits in handling properties and ultimate cure material physical properties. In some embodiments, at least some of the polymerizable component is lower in viscosity relative to the other ingredients of the composition thus functioning to lower the viscosity of the overall uncured composition. One skilled in the art can vary the viscosity of the uncured composition depending on its intended application.

The suitablility of a polymerizable component can depend on which side it resides. When it resides in part A, useful polymerizable components include: (i) partially water soluble monomers, (ii) non-hydroxylic functional monomers that are partially water soluble (such as polyethylene glycol dimethacrylate and tetrahydrofurfuryl methacrylate), or (iii) longer chain hydroxylic functional monomers that do not fully solubilize the polyacid and/or the redox catalyst. Of these, the non-hydroxylic functional monomers are preferred. The polymerizable components of Part A are preferably partially or fully water soluble.

When residing in part B, the polymerizable component can be any monomer that, when combined with water, generate a single liquid phase. This criteria does not imply that any individual monomer has to be water soluble, but that a combination of monomers be water soluble. Examples of suitable polymerizable component include 2-hydroxyethyl methacrylate (HEMA), glycerol dimethacrylate (GDMA), and glycerol monomethacrylate (GMMA).

Other suitable polymerizable components include monomers that contain acid functionality. Illustrative examples include the bis-isocyanatoethylmethacrylate derivative of bis-hydroxymethylpropionic acid (PDMA) or the bis-isocyanatoethylmethacrylate derivative of citric acid (CDMA). Unlike the polyacids described above, which preferably exist as partially or fully dispersed components, these acid-functionalized polymerizable components may be fully dissolved in the polymerizable components such as polyethylene glycol dimethacrylate and tetrahydrofurfural methacrylate. These acid-functionalized polymerizable components, however, do not contain hydroxyl functionality, particularly primary or secondary hydroxyl functionality. They contain multiple polymerizable groups and can participate in several types of curing chemistry such as the glass ionomer chemistry and the free radical initiated polymerization chemistry. They can be used to enhance various physical and handling properties of the inventive composition. When used they constitute from about 1 to 35 parts of the total composition.

Fillers

Two general classes of fillers are used in the present invention: reactive fillers and non-reactive fillers. The fillers can reside in either part A and/or part B. Regardless of the type of filler used, it should be non-toxic and suitable for use in the mouth. The filler can be radiopaque or non-radiopaque.

Suitable reactive fillers for use in the present inventive cement include those that are commonly used with glass ionomer cements. Illustrative examples of suitable reactive fillers include metal oxides such as zinc oxide and magnesium oxide, and non-leachable glasses, such as those described in U.S. Pat. Nos. 3,655,605; 3,814,717; 4,143,018; 4,209,434; 4,360,605; and 4,376,835.

Preferably the reactive filler is finely divided so that it can be mixed conveniently with other ingredients and used in the mouth. The average particle diameter for the filler is about 0.2 to 15 micrometers, preferably about 0.2 to 10 micrometers, as measured using, e.g., a sedimentation analyzer.

Preferred reactive fillers are acid-reactive. Suitable acid-reactive fillers include metal oxides, metal salts, and glasses. Preferred metal oxides include the oxides of barium, calcium, magnesium, and zinc. Preferred metal salts include salts of multivalent cations, e.g., aluminum acetate, aluminum chloride, calcium chloride, magnesium chloride, zinc chloride, aluminum nitrate, barium nitrate, calcium nitrate, magnesium nitrate, strontium nitrate, and calcium fluoroborate. Preferred glasses include borate glasses, phosphate glasses, and fluoroaluminosilicate glasses (FAS), the last being particularly preferred. Various forms of calcium phosphates such as hydroxyapatite ($Ca_{10}$ $(PO_4)_6$ $(OH)_2$) or monetite ($CaHPO_4$) can also be used. Another preferred reactive filler is the class of bioactive glasses and glass-ceramics, which are believed to attach directly by chemical bonding to bone and other biological tissues. Examples of such materials are disclosed in U.S. Pat. No. 5,074,916. Mixtures of these reactive fillers can be used.

If desired, the reactive filler can be subjected to surface treatment as described in U.S. Pat. No. 6,136,885, e.g., at column 8, lines 35 to 42. The surface of the reactive filler can be treated with a coupling agent. Suitable coupling agents include gamma-methacryloxypropyltrimethoxysilane, gamma-mercaptopropyltriethoxysilane, gamma-aminopropyltrimethoxysilane, and the like.

The amount of reactive filler used should be sufficient to provide a composition having desirable mixing and handling properties before cure and good performance after cure. The reactive filler represents less than about 90%, preferably about 15% to 75%, more preferably about 30% to 60% by weight of the total weight of the composition.

As stated above, non-reactive fillers can be used in the present invention. Non-reactive fillers can be selected from one or more of any material suitable for use in medical applications. The filler is finely divided and preferably has a maximum particle diameter less than about 50 micrometers and an average particle diameter less than about 10 micrometers. The filler can have a unimodal or polymodal (e.g., bimodal) particle size distribution. The filler can be an inorganic material. It can also be a crosslinked organic material that is insoluble in the polymerizable component.

Illustrative examples of suitable non-reactive inorganic fillers are naturally occurring or synthetic materials such as quartz, nitrides (e.g., silicon nitride), glasses derived from, e.g., Ce, Sb, Sn, Zr, Sr, Ba, and Al. Other glasses include colloidal silica, feldspar, borosilicate glass, kaolin, talc, titania, and zinc glasses. Also useful are low Mohs hardness fillers such as those described in U.S. Pat. No. 4,695,251 and submicron silica (e.g., pyrogenic silicas such as the AEROSIL series OX 50, 130, 150, and 200 silicas commercially available from Degussa Co., Germany and CAB-O-SIL M5 silica sold by Cabot Corp., Tuscola, Ill.). Illustrative examples of suitable non-reactive organic filler particles include filled or unfilled pulverized polycarbonate, polyepoxides, and the like. Alloys of silver, copper or tin can also be used as non-reactive fillers. Mixtures of the non-reactive fillers can also be used.

Redox Catalysts

A preferred mode of initiating the polymerization reaction uses oxidizing and reducing agents as a redox catalyst system. The catalyst enables the ionomer cement composition to cure via a redox reaction. The oxidizing and reducing agents can reside in either parts A or B. These agents can exist in a disperse phase. Preferably, the oxidizing agent exists as a disperse phase in part A and the reducing agent is soluble in part B, although the reducing agent can exist as a disperse phase in part B. Various redox catalyst systems and their use in ionomer cements are described in U.S. Pat. No. 5,154,762, e.g., at column 5, line 32 to column 6, line 13. If desired, the reducing and/or oxidizing agents can be microencapsulated, as described in U.S. Pat. No. 5,154,762, e.g., at column 6, line 13 to column 7, line 11.

The oxidizing agent should react with or otherwise cooperate with the reducing agent to produce free radicals. The free radicals are capable of initiating polymerization of the ethylenically unsaturated moiety, which may possibly be present from the polyacid and/or from the polymerizable component. The oxidizing and reducing agents preferably are present in an amount sufficient to permit an adequate free radical reaction rate. For example, in one embodiment, the inventive composition can comprise from about 0.1 to 5.0 parts oxidizing agent, and from about 0.05 to 5.0, preferably about 0.05 to 3.0 parts reducing agent, based on the total weight of the composition.

Suitable oxidizing agents include persulfates such as sodium, potassium, ammonium, and alkyl ammonium persulfates. Other suitable oxidizing agents include peroxides, such as benzoyl peroxide and lauroyl peroxide, and hydroperoxides such as cumene hydroperoxide, tert-butyl hydroperoxide, tert-amyl hydroperoxide, and 2,5-dihydroperoxy-2,5-dimethylhexane. Yet other suitable oxidizing agents include salts of cobalt (III), iron (III), terium (IV), copper (II), perboric acid and its salts, and salts of a permanganate anion. Combinations of the oxidizing agents can be used.

Suitable reducing agents include amines (preferably aromatic amines), ascorbic acid, metal complexed ascorbic acid, cobalt (II) chloride, ferrous chloride, ferrous sulfate, hydrazine, hydroxylamine, oxalic acid, thiourea and derivatives thereof, barbituric acid and derivatives thereof, and salts of dithionite, thiosulfate, sulfite anion, and aromatic sulfinates, such as benzene sulfinate and toluene sulfinate.

Photoinitiators

The inventive cement system may contain one or more suitable photoinitiators that act as a source of free radicals when activated. The photoinitiators can reside in part A and/or part B. Such initiators can be used alone or in combination with one or more accelerators and/or sensitizers.

The photoinitiator should be capable of promoting free radical crosslinking of the ethylenically unsaturated moiety on the polymerizable component and/or the polyacid on exposure to light of a suitable wavelength and intensity. The photoinitiator should be shelf stable and free of undesirable coloration, thereby allowing it to be stored and used under typical dental conditions. Visible light (about 400 to 800 nm wavelength) photoinitiators are preferred. The photoinitiator is preferably partially or fully water soluble or water miscible. Photoinitiators having polar groups usually have a sufficient degree of water solubility or water miscibility. The photoinitiator frequently can be used alone. Typically, however, it is used in combination with a suitable donor compound or a suitable accelerator (e.g., amines, peroxides, phosphorous compounds, ketone and alpha-diketone compounds).

Suitable visible light-induced initiators include camphorquinone, which is typically combined with a suitable hydrogen donor. Other suitable visible light-induced initiators include diaryliodonium simple or metal complex salts, chromophore-substituted halomethyl-s-triazines and halomethyl oxadiazoles. Preferred candidates include combinations of an alpha-diketone, e.g., camphorquinone, and a diaryliodonium salt, e.g., diphenyliodonium chloride, bromide, iodide or hexafluorophosphate, with or without additional hydrogen donors (such as sodium benzene sulfinate, amines, and amine alcohols). Other suitable visible light initiator systems may include alternative sensitizers compounds such as fluorone dyes, ketocoumarins, and the like.

Free-radical initiators useful in the invention, e.g., those that are photochemically active in the wavelength region of greater than 400 to 800 nm, also may include the class of acylphosphine oxides, as described in European Patent Application No. 173567. Such acylphosphine oxides are of the general formula

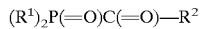

$(R^1)_2P(=O)C(=O)-R^2$ wherein each $R^1$ individually can be a hydrocarbyl group such as alkyl, cycloalkyl, aryl, and aralkyl, any of which can be substituted with a halo-, alkyl- or alkoxy-group, or the two $R^1$ groups can be joined to form a ring along with the phosphorous atom, and wherein $R^2$ is a hydrocarbyl group, an S-, O-, or N-containing five- or six-membered heterocyclic group, or a $-Z-C(=O)-P(=O)-(R^1)_2$ group, wherein Z represents a divalent hydrocarbyl group such as alkylene or phenylene having from 2 to 6 carbon atoms.

Preferred acylphosphine oxides useful in the invention are those in which the $R^1$ and $R^2$ groups are phenyl or lower alkyl- or lower alkoxy-substituted phenyl. By "lower alkyl" and "lower alkoxy" is meant such groups having from 1 to 4 carbon atoms. Most preferably, the acylphosphine oxide is bis(2,4,6-trimethylbenzoyl)phenyl phosphine oxide (IRGACURE 819, Ciba Specialty Chemicals, Tarrytown, N.Y.).

Preferred ultraviolet light induced photoinitiators include ketones such as benzyl and benzoin, and acyloins and acyloin ethers. Preferred commercially available candidates include IRGACURE 651, which is 2-dimethoxy-2-phenylacetophenone, and benzoin methyl ether (or 2-methoxy-2-phenylacetophenone), both from Ciba-Geigy Corp., Basel, Switzerland.

The photoinitiator should be present in an amount sufficient to provide the desired rate of photopolymerization. This amount will depend in part on the light source, the cement layer thickness that will be exposed to the light source, and the extinction coefficient of the photoinitiator. Typically, the photoinitiator is present at about 0.005% to 5%, preferably about 0.05% to 1% by weight, based on the total weight of the composition.

For photocurable ionomers that are polymerized by a cationic mechanism, suitable initiators include salts that are capable of generating cations such as the diaryliodonium, triarylsufonium, and aryldiazonium salts.

Advantageously, having three cure mechanisms in the inventive cement (photocure, dark cure through a redox reaction, and ionic cure) facilitates thorough, uniform cure. Cements using three modes of cure have particular utility in clinical applications where cure of a conventional light-curable composition may be difficult to achieve. Such applications include, e.g., deep restorations, large crown build-ups, endodontic restorations, luting of metallic crowns or other light-impermeable prosthetic devices to teeth, and other restorative applications in inaccessible areas of the mouth.

Miscellaneous Components

The inventive composition may optionally comprise additional adjuvants suitable for use in the oral environment, including colorants, inhibitors, accelerators, flavorants, antimicrobials, fragrance, stabilizers (including free radical stabilizers), viscosity modifiers, submicron silica particles, and modifiers or additives that impart fluorescence and/or opalescence.

Modifying agents prolonged working time. The term "working time" refers to the time between the beginning of the setting reaction in a restoration and the time sufficient hardening has occurred to allow subsequent clinical procedures to be performed on the surface of the restoration. Useful modifying agents include, e.g., alkanolamines such as ethanolamine and triethanolamine, and mono-, di-, and tri-sodium hydrogenphosphates. Modifying agents can be added to either part A or part B. When used, they are present at a concentration between about 0.1 to 10 percent by weight, based on the total composition weight.

Stabilizers provide color stability. Suitable stabilizers include oxalic acid, sodium metabisulfite, sodium bisulfite, sodium thoisulfate, metaphosphoric acid, and combinations thereof.

Free radical stabilizers can be used with the photoinitiator to prevent premature polymerization or to adjust the working time in free radical systems. Suitable examples of free radical stabilizers include, e.g., butylated hydroxytoluene (BHT) and methyl ethyl hydroquinone (MEHQ).

Submicron silica particles improve the handling properties. Suitable silica particles include pyrogenic silicas such as AEROSIL series OX 50, 130, 150, 200, and R-812S, available from Degussa Corp., and CAB-O-SIL M5 silica available from Cabot Corporation.

In one embodiment, the invention is conveniently provided in the form of a kit. In the kit, part A and part B can be provided in a variety of containers, such as tubes, syringes, bottles, dual barrel syringes, auto-mix systems, titurable capsules, and foil packages. An illustrative kit contains a dual barrel syringe having a first barrel and a second barrel. Part A resides in the first barrel and Part B resides in the second barrel. Part A is a dispersion that comprises, e.g., at least one polyacid, at least one polymerizable component, and an oxidizing agent, where the polyacid and/or the oxidizing agent is dispersed in the polymerizable component. Part B comprises water, reactive fillers, and at least one reducing agent where the reducing agent can be dispersed in polymerizable component. In use, a portion of parts A and B, would be dispensed onto a mixing pad. The user would mix the two parts together, typically by hand, and apply the composition to a patient's dental structure. The kit may optionally contain items, including but not limited to, instructions, adhesive systems, restorative material, instruments, mix pads, prosthesis, or other materials used in a dental procedure.

EXAMPLES

The following examples are provided to illustrate different embodiments and details of the invention. Although the examples serve this purpose, the particular ingredients and amounts used as well as other conditions and details are not to be construed in a manner that would unduly limit the scope of this invention. Unless otherwise specified, all percentages are in weight percent.

TABLE 1

COMPONENTS USED IN CEMENT FORMULATIONS

| Components | Abbreviations |
|---|---|
| Aerosil R-812S | non-reactive fillers (Degussa, Germany) |
| Aerosil 200 | non-reactive fillers (Degussa, Germany) |
| A-174 | 3-methacryloxypropyltrimethoxysilane (Witco Co., South Charleston, WV) |
| BHMPA | 2,2-bis(hydroxymethyl)propionic acid |
| BHT | butylated hydroxytoluene or 2-6-di-tert-butyl-4-methylphenol |
| BPO | benzoyl peroxide (Aldrich Chemical Co., Milwaukee, WI) |
| CDMA | citric acid dimethacrylate |
| CSF | calcinated silica filler, 6000 RST-M (Quarzwerke GMBH, Germany) |
| DBTDL | dibutyltin dilaurate |
| DI $H_2O$ | de-ionized water |
| FAS Glass | flouroaluminosilicate glass, reactive filler |
| GDMA | glycerol dimethacrylate |
| HEMA | 2-hydroxyethyl methacrylate |
| IEM | ioscyanatoethylmethacrylate |
| MFPA | methacrylated functional polycarboxylic acid, made according to Example 11 of U.S. Pat. No. 5,130,347 |
| OX-50 | fumed silica (Degussa, Germany) |
| PEGDMA | polyethylene glycol dimethacrylate, MW about 400 (Rohm-Tech: MFM-409) |
| PDMA | bis(hydroxymethyl)propionic acid di(N-methacryloxyethyl)carbamate |
| t-BDMA | 4-tert-butyl-N N-dimethylaniline |
| TEGDMA | triethyleneglycol dimethacrylate |
| THF | dry tetrahydrofuran (water content <0.02%) |
| TPS | triphenyl antimony |
| Zr—Si | zirconia-silica filler |

Benzoyl Peroxide Determination by Potentiometer Titration Test

For determining the amount of benzoyl peroxide remaining in a sample after storage, a titrator with the capability of potentiometric titration (such as CH-8606, available from Mettler-Toledo AG, Greifensee, Switzerland) with a combination platinum/silver-silver chloride electrode was used. The manufacturer's procedures were followed to determine the amount of benzoyl peroxide remaining over selected time intervals. For each example, a sample of about 2.5 gram was titrated. The titration procedure was replicated three times for each example and an average value was to calculate the percent BPO.

To each sample, 30 mL of acetonitrile was added and sonicated for 1 to 2 minutes. A 5 mL portion of a 20% (weight/volume) of potassium iodide was added to the sample and stirred for 1 minute. The liberated iodide was titrated with a 0.1 N sodium thiosulfate titrant. The percent of benzoyl peroxide present in the sample was calculated using the following formula:

$$\text{Percent benzoyl peroxide} = ((T_{vol} - \text{Blank}) \times (12.11) \times (100)) \div W_{sample}$$

$T_{vol}$=volume of sodium thiosulfate titrant used to titrate the sample (in mL);
Blank=volume of sodium thiosulfate titrant used to titrate a blank sample (in mL);
12.11=a conversion factor, 1 mL of 0.1 N sodium thiosulfate is equivalent to 12.11 mg of benzoyl peroxide; and
$W_{sample}$=sample weight in milligrams.

Adhesion to Dentin Test

Adhesive strength to dentin for the examples tested was evaluated by the following procedure. For each example composition, five bovine teeth of similar age and appearance were partially embedded in circular acrylic discs. The exposed portion of each tooth was ground flat and parallel to the acrylic disc using Grade 120 silicon carbide paper-backed abrasive mounted on a lapidary wheel, in order to expose the dentin or enamel. During this and subsequent grinding and polishing steps, the teeth were continuously rinsed with water. Further grinding and polishing of the teeth was carried out by mounting Grade 600 silicon carbide paper-backed abrasive on the lapidary wheel.

The polished teeth were stored in deionized water and used for testing within 2 hours after polishing. Previously made molds of 2 mm thick Teflon™ sheet with a 5 mm diameter hole punched through the sheet were filled with Z100™ composite (3M Co., St. Paul, Minn.). The Z100™ composite in the 2 mm×5 mm mold was exposed for 60 seconds to radiation from a Visilux-2 dental curing light (3M Co., St. Paul, Minn.). The Z100™ test button was removed from the mold and one side of the button was roughened with 320 grit sandpaper. The polished teeth were removed from the water and blotted dry. In a controlled environment of 25° C. and 50% relative humidity and within one minute of mixing of an example composition, a layer of the composition was applied with a spatula to the roughened side of the Z100™ button. The button with the cement was pressed onto the tooth surface to create an assembly. The assembly was allowed to stand for an additional minute. Thereafter, the entire assembly was placed in a humidity chamber set at 97% relative humidity and 37° C. for 15 minutes. From the humidity chamber, the assembly moved into 37° C. deionized water for 24 hours.

The strength of the cured cement examples was evaluated by mounting the assembly in a holder clamped in the jaws of an Instron™ (Instron 4505, Instron Corp. Canton, Mass.) with the polished tooth surface oriented parallel to the direction of pull. A loop of orthodontic wire (0.44 mm diameter) was placed around the Z100™ button adjacent to the polished tooth surface. The end of the orthodontic wire were clamped in the pulling jaw of the Instron apparatus, thereby placing the bond in shear stress. The bond was stressed until it (or the dentin or the formulation) failed, using a crosshead speed of 2 mm/min.

Diametral Tensile Strength (DTS) and Compressive Strength (CS) Tests

ADA (American Dental Association) specification No. 9 and ADA specification No. 27 of ISO test procedure 4049 (1988) were followed for all DTS and CS testing. In particular, each sample was packed into a 5 mm (inside diameter) glass tube, capped with silicone rubber plugs, and axially compressed at about 0.28 MPa for 20 minutes. The samples were self-cured. The samples were stored in distilled water at 37° C. for about 24 hours prior to testing. The cured samples were cut on a diamond saw forming cylindrical samples 8 mm and 2 mm long, for CS and DTS testing respectively. DTS and CS values for each sample were measured using a Instron 4504, available from Instron Corp., Canton, Mass.

For CS, the samples were tested using a 10 kN load cell. A total of 4 to 5 cylinders were tested for each sample. For DTS, the samples were tested also using a 10 kN load cell. A total of 5 to 7 cylinders were tested for each sample.

Preparation of PDMA

PDMA was synthesized according to the following procedure. Into a reaction vessel equipped with mechanical stirrer, condenser, and addition funnel was charged BHMPA (225 g, 1.68 mole), BHT (1.68 g, 7.62 mmole), TPS (1.35 g, 3.81 mmole), DBTDL (2.44 g, 3.86 mmole), and about 1000 mL THF. Thereafter, IEM (593 g, 3.82 mole) was added over about 30 minutes. The reaction was heated to 65° C. for about 30 hours with constant stirring. Then, the THF was stripped off under 20 to 40 mm Hg vacuum. The final product, PDMA, was a colorless, viscous liquid.

Preparation of CDMA

In a reaction vessel fitted with a mechanical stirrer, condenser, addition funnel, and air inlet tube, 400 g of citric acid was dissolved in 2 L of dry THF. To the resultant homogeneous solution was added 0.52 g BHT, 0.5 g TPS, and 0.98 g DBTDL. Dry air was added to the reaction mixture through the inlet tube. Then, 161.5 g (1.04 moles) of IEM was added dropwise through the addition funnel so as to maintain a reaction temperature of about 40° C. The reaction was followed by infrared spectroscopy. After all of the IEM had been added and the IR spectrum no showed little to no isocyanate group, the THF was removed under vacuum from the reaction mixture. The resultant viscous liquid was dried. Nuclear magnetic resonance spectroscopy showed the presence of added methacrylate groups and the retention of carboxy groups.

Preparation of FAS Glass

Untreated FAS glass (commonly referred to as "glass frit") was screened through a 60 micrometer mesh. The FAS glass had the following formulation: 37 parts $SiO_2$, 23 parts $AlF_3$, 20 parts SrO, 10 parts $Al_2O_3$, 7 parts $AlPO_4$, 6 parts $Na_3AlF_6$, and 4 parts $P_2O_5$. The FAS glass was ball-milled to provide a pulverized frit having a surface area of 2.5 to 3.2 $m^2/g$ using the Brunauer, Emmet, Teller (BET) test method.

In a 60-gallon ball mill, 233 kg of clean 1.27×1.27 cm (0.5×0.5 inch) ceramic media was added to the mill. A 20 kg portion of the pulverized glass frit (from above) and 200 grams of ethanol were weighed and added to a stainless steel pitcher. The ball mill was purged with nitrogen for 10 minutes. After the frit was milled for 3.5 hours, the mill was cooled down and purged with nitrogen for 10 minutes. The mill material was discharged and passed through a 400 micrometer screen. The screened frit was charged to a PK blender (Patterson-Kelly Corp., Stroudsberg, Pa.) and blended for 30 minutes.

Preparation of Zr—Si Filler

Zirconia-silica filler was prepared as follows. In a first vessel, 25.5 parts silica sol (LUDOX LS, E. I. duPont de Nemours & Co., Wilmington, Del.) was acidified by the rapid addition of 0.255 parts concentrated nitric acid. In a separate vessel, 12.9 parts ion-exchanged zirconyl acetate (Magnesium Elektron, Inc., Flemington, N.J.) were diluted with 20 parts deionized water and the resultant solution acidified with 0.255 parts concentrated nitric acid. The silica sol was pumped into the stirred zirconyl acetate solution and mixed for one hour. The stirred mixture was filtered through a 3 micrometer filter followed by a 1 micrometer filter. The filtrate was poured into trays to a depth of about 25 mm and dried at 65° C. in a forced air oven for about 35 hours. The resultant dried material was removed from the oven and tumbled through a rotary tube furnace (Harper Furnace Corp.) previously preheated to 950° C. to produce calcined material.

Into a tumbling ball mill was charged 75 parts calcined material, 3 parts methanol, 1.9 parts benzoic acid, and 1.1 parts deionized water with 6.35 mm (0.25 inch) alumina media to comminute the calcined material to an average particle size of 0.05 to 0.2 micrometers (as measured using a Micromeritics 5100 sedigraph). The filler was then loaded into ceramic saggers and fired in an electric furnace (L&L Furnace Corp.) at air temperature of 880° to 900° C. for approximately 8 hours. The fired filler was then ball-milled for 4 to 5 hours, where the mill charge included 32 parts fired filler, 1.25 parts ethanol, and 0.3 parts deionized water. The filler was passed through a vibratory screener (Vortisiv V/S 10010, VORTIS-SIV Division of MM Industries, Inc., Salem, Ohio) equipped with a 74 micrometer nylon screen. The filler was then blended in a V-blender (Patterson-Kelly Corp., Stroudsberg, Pa.) for 15 minutes.

The cooled microparticles were slurried in hydrolyzed A-174 silane, dried in a forced air oven, and screened through a 74 micrometer screen. The treated filler particles contained 11.1% silane.

Preparation of Silanol Treated Fumed Silica

A silanol solution was prepared by mixing together 16.48 parts of A-174, 10.99 parts of methanol, 1.49 parts of acetic acid, and 2.39 parts of deionized water. During mixing the silanol solution was kept in a temperature range of 20° C. to 30° C. Fumed silica (OX-50) (68.66 parts) was charged to a V-blender. While mixing the fumed silica, the silanol solution was pumped into the V-blender over the course of 30 minutes. The treated powder was discharged from the V-blender blender into plastic-lined trays, and dried for three hours, 45 minutes at 67° C. and then for one hour, 15 minutes at 100° C. The treated dried powder was sieved through a 74 micrometer screen.

Examples 1 and 2

Examples 1 and 2 exemplify two paste-paste compositions of this invention. Each example comprised a nonaqueous paste with a dispersed polyacid (part A) and an aqueous paste (part B). The A and B pastes were prepared by combining and mixing the respective components listed in Table 2. Each example was prepared by transferring 0.2 gram of part A and 0.2 gram of part B to a dental mixing pad and mixing the components by hand with a spatula.

TABLE 2

| Components | Example 1 | Example 2 |
| --- | --- | --- |
| Part A: | | |
| PEGDMA | 19.9 | 42.7 |
| PDMA | 27.0 | 0 |
| TEGDMA | 3.0 | 0 |
| BPO | 0.8 | 1.5 |
| BHT | 0.05 | 0.05 |
| MFPA | 8.4 | 23.3 |
| Aerosil R-812S | 2.9 | 3.6 |
| Zr—Si | 3.6 | 28.8 |
| Part B: | | |
| water | 14.9 | 30.0 |
| HEMA | 0 | 20.0 |
| PEGDMA | 34.7 | 0 |
| t-BDMA | 0.4 | 0.6 |
| Aerosil 200 | 5.0 | 5.0 |
| FAS glass | 45.1 | 44.4 |
| RESULTS: | | |
| DTS (MPa) | 17.9 | 13.8 |
| CS (MPa) | 69.6 | 41.4 |
| Adhesion (MPa) | 0 | 4.8 |

The data in Table 2 showed that Examples 1 and 2 had adequate performance to function as a dental composition, particularly for use as a resin modified glass ionomer cement.

Examples 3 to 9

Examples 3 to 9 exemplify different formulations of Part A. The components, as listed in Table 3, were mixed together in a vessel and tested for percent BPO remaining for a minimum of four times for up to 15 months. The % BPO remaining was plotted as a function of storage time and the slope of the line was obtained from linear regression. The regression curves had correlation coefficients greater than 0.87. The slope values were a negative number, indicating a loss of BPO. A larger negative slope corresponded to a greater loss in BPO amount. In general, as the slope approached zero, there was less loss of BPO over time. This condition indicated that the BPO was more stable in the composition translating to a storage stable composition.

Table 3 reported the percent BPO remaining at three and six months. These values were interpolated from the linear regression curves.

Example 3 exemplified a composition containing a polyacid (MFPA) as a disperse phase in the polymerizable components. Examples 4 to 6 exemplified compositions where a monoacid (PDMA) was dissolved in the polymerizable component and no polyacid was used. The PDMA monoacid did not have hydroxyl functional groups. Example 7 exemplified a combination of the MFPA polyacid as a disperse phase in the polymerizable components and the PDMA monoacid dissolved in the polymerizable components. Examples 8 and 9 exemplified compositions containing a combination of the MFPA polyacid as a disperse phase in the polymerizable components and the PDMA monoacid dissolved in the polymerizable components.

samples were tested for percent BPO remaining four times over the course of four months. The %BPO values remaining were plotted as a function of storage time and the slope of the line was obtained from linear regression. The regression curves had correlation coefficients greater than 0.97. Table 4 reported the amount of BPO remaining at three months, which was interpolated from the regression curve, and at six months, which was extrapolated from the regression curve.

TABLE 4

| Components | Comparative A | Comparative B | Comparative C |
|---|---|---|---|
| Part A: | | | |
| PEGDMA | 38.22 | 14.34 | 27.66 |
| PDMA | 0 | 0 | 0 |
| TEGDMA | 0 | 0 | 0 |
| GDMA | 0 | 0 | 0 |
| CDMA | 0 | 0 | 41.48 |
| BPO | 0.64 | 0.65 | 1.38 |
| BHT | 0.05 | 0.06 | 0.07 |
| MFPA | 19.12 | 23.9 | 0 |
| Aerosil R-812S | 2.50 | 2.51 | 0 |
| CSF | 0 | 0 | 0 |
| OX-50 | 0 | 0 | 29.4 |
| Zr—Si filler | 34.72 | 34.64 | 0 |
| DI $H_2O$ | 4.75 | 23.9 | 0 |
| RESULTS: | | | |
| % BPO (3 mth) | 42 | 33 | 77 |
| % BPO (6 mth) | 0 | 0 | 56 |
| Slope | −0.2013 | −0.1897 | −0.0688 |

TABLE 3

| | Example 3 | Example 4 | Example 5 | Example 6 | Example 7 | Example 8 | Example 9 |
|---|---|---|---|---|---|---|---|
| Components Part A: | | | | | | | |
| PEGDMA | 45.01 | 13.83 | 13.83 | 11.75 | 11.75 | 23.50 | 23.50 |
| PDMA | 0 | 49.16 | 49.16 | 42.31 | 42.31 | 0 | 0 |
| TEGDMA | 0 | 0 | 6.15 | 0 | 4.70 | 0 | 0 |
| GDMA | 0 | 6.15 | 0 | 4.70 | 0 | 0 | 0 |
| CDMA | 0 | 0 | 0 | 0 | 0 | 35.26 | 35.26 |
| BPO | 1.01 | 1.38 | 1.38 | 1.18 | 1.18 | 1.18 | 1.18 |
| BHT | 0.07 | 0.07 | 0.071 | 0.06 | 0.06 | 0.06 | 0.06 |
| MFPA | 20.0 | 0 | 0 | 0 | 15.0 | 15.0 | 15.0 |
| Aerosil R-812S | 0.96 | 0 | 0 | 0 | 0 | 0 | 0 |
| CSF | 0 | 0 | 0 | 25.0 | 25.0 | 25.0 | 0 |
| OX-50 | 0 | 29.4 | 29.4 | 0 | 0 | 0 | 0 |
| Zr—Si filler | 33.0 | 0 | 0 | 0 | 0 | 0 | 25.0 |
| RESULTS: | | | | | | | |
| % BPO (3 mth) | 100 | 88 | 89 | 91 | 93 | 84 | 80 |
| % BPO (6 mth) | 96 | 83 | 83 | 84 | 88 | 70 | 65 |
| Slope | −0.0139 | −0.019 | −0.018 | −0.0245 | −0.0178 | −0.0454 | −0.0481 |

Example 10

This example exemplified a paste-paste composition where a redox catalyst, specifically an oxidizing agent, is in a disperse phase. Part A was prepared by combining and mixing the following components in a vessel, all parts being parts by weight: 15.3 parts HEMA, 3.5 parts potassium persulfate, 0.03 part BHT, 6.4 parts copolymer of acrylic acid and itaconic acid, 6.4 parts MFPA, and 6.1 parts Zr—Si filler. Part B was prepared by combining and mixing the following components in a vessel: 18.9 parts deionized water, 3.5 parts sodium para-toluenesulfinate, and 39.8 parts FAS glass. Parts A and B were transferred to a mixing pad and mixed by hand with a spatula to yield the resulting dental composition.

Comparative Examples A to C

Comparative Examples A to C were made by mixing the components listed in Table 4 together in a vessel. The Comparative Examples A and B exemplified compositions where the polyacid (MFPA) is dissolved in an aqueous polymerizable component. The comparative data showed that no BPO is projected to remain after six months of storage, a result of the large negative slope values. A general comparison of the slope values indicated that Examples 3 to 7 lost BPO about one-tenth as fast as Comparative Examples A and B.

Comparative Example C exemplified a composition containing a monoacid (CDMA) dissolved in the polymerizable component. The CDMA monoacid had an attached tertiary hydroxyl group. This example, however, did not contain any polyacid dispersed in the polymerizable component.

All references cited herein are incorporated by reference in each reference's entirety.

What is claimed is:

1. A dental composition comprising:
   (a) a part A comprising discrete, solid particles of a polymer comprising acid functionality dispersed in a polymerizable component; and
   (b) a part B comprising water;
   wherein the composition further comprises an oxidizing agent, a reducing agent, and a reactive filler in at least one of part A and part B.

2. The dental composition of claim 1 wherein part A further comprises discrete particles of the oxidizing agent dispersed in the polymerizable component and part B further comprises the reactive filler and the reducing agent.

3. The dental composition of claim 2 wherein the polymerizable component is selected from the group consisting of (i) partially water soluble monomers, (ii) non-hydroxylic functional monomers that are partially water soluble, and (iii) hydroxylic functional monomers that do not fully solubilize the polymer comprising acid functionality and/or the redox catalyst.

4. The dental composition of claim 2, wherein the polymerizable component is selected from the group consisting of polyethylene glycol dimethacrylate, tetrahydrofurfuryl methacrylate, triethyleneglycol dimethacrylate, and combinations thereof.

5. The dental composition of claim 1 comprising about 5 to about 30 parts polymer comprising acid functionality, based on the total weight of the composition.

6. The dental composition of claim 5, wherein the polymer comprising acid functionality is derived from monomers selected from the group consisting of acrylic acid, methacrylic acid, itaconic acid, maleic acid, glutaconic acid, aconitic acid, citraconic acid, mesaconic acid, fumaric acid, and tiglic acid, and combinations thereof.

7. The dental composition of claim 1 comprising about 5 to about 75 parts polymerizable component, based on the total weight of the composition.

8. The dental composition of claim 1 comprising about 0.1 to about 5.0 parts oxidizing agent, based on the total weight of the composition.

9. The dental composition of claim 8 wherein the oxidizing agent is selected from the group consisting of sodium persulfate, potassium persulfate, ammonium persulfate, alkyl ammonium persulfate, benzoyl peroxide, lauroyl peroxide, cumene hydroperoxide, tert-butyl hydroperoxide, tert-amyl hydroperoxide, 2,5-dihydroperoxy-2,5-dimethylhexane, perboric acid and its salts, salts of a permanganate anion, salts of cobalt (III), iron (III), terium (IV), copper (II), and combinations thereof.

10. The dental composition of claim 1 comprising about 5 to about 35 parts water, based on the total weight of the composition.

11. The dental composition of claim 1, wherein the reactive filler is selected from the group consisting of fluoroaluminosilicate glass, borate glass, phosphate glass, hydroxyapatite, hydroxymonetite, and combinations thereof.

12. The dental composition of claim 1 comprising about 25 to about 65 parts reactive filler based on the total weight of the composition.

13. The dental composition of claim 1 comprising about 0.05 to about 3.0 parts reducing agent based on the total weight of the composition.

14. The dental composition of claim 1 wherein parts A and B are miscible upon mixing.

15. The dental composition of claim 1 wherein the composition forms a material selected from the group consisting of dental adhesives, anterior filling materials, posterior filling materials, casting materials, cavity liners, cements, coating compositions, adhesives and cements for affixing orthodontic brackets and appliances, endodontic cements, restoratives, and sealants.

16. A dental composition comprising:
   (a) a part A comprising bis(hydroxymethyl)propionic acid di(N-methacryloxyethyl)carbamate dissolved in a polymerizable component; and
   (b) a part B comprising water;
   wherein the composition further comprises an oxidizing agent, a reducing agent, and a reactive filler in at least one of part A and part B.

17. A dental composition comprising:
   (a) a part A comprising bis(hydroxymethyl)propionic acid di(N-methacryloxyethyl)carbamate dissolved in a polymerizable component selected from the group consisting of polyethylene glycol dimethacrylate, glycerol dimethacrylate, triethyleneglycol dimethacrylate, and combinations thereof; and
   (b) a part B comprising water;
   wherein the composition further comprises an oxidizing agent, a reducing agent, and a reactive filler in at least one of part A and part B.

18. A kit comprising the dental composition of claim 1 provided in a container selected from the group consisting of tubes, syringes, bottles, dual barrel syringes, auto-mix systems, titurable capsules, foil packages, and combinations thereof.

19. The kit of claim 18 further comprising at least one component selected from the group consisting of instructions, adhesive systems, restorative material, instruments, mix pads, prosthesis, and other materials used in a dental procedure.

20. A kit comprising:
   (a) a dual barrel syringe having a first barrel and a second barrel, wherein the dental composition of claim 1 is stored in the barrels such that part A resides in the first barrel and part B resides in the second barrel; and
   (b) instructions to use the syringe.

21. A dental composition comprising:
   (a) a part A comprising a polymerizable component and a polymer comprising acid functionality; and
   (b) a part B comprising water;
   wherein the composition further comprises an oxidizing agent, a reducing agent, and a reactive filler in at least one of part A and part B; and
   wherein at least one of the oxidizing agent and the reducing agent comprises non-microencapsulated discrete articles dispersed in part A or part B.

22. A method of preparing a dental material comprising combining:
   a part A comprising discrete, solid particles of a polymer comprising acid functionality dispersed in a polymerizable component; and a part B comprising water;

wherein the composition further comprises an oxidizing agent, a reducing agent, and a reactive filler in at least one of part A and part B.

23. The method of claim 22 further comprising applying the dental material to a dental structure.

24. A method of preparing a dental material comprising combining:

a part A comprising a polymerizable component and a polymer comprising acid functionality; and a part B comprising water;

wherein the composition further comprises an oxidizing agent, a reducing agent, and a reactive filler in at least one of part A and part B; and wherein at least one of the oxidizing agent and the reducing agent comprises non-microencapsulated discrete particles dispersed in part A or part B.

* * * * *

UNITED STATES PATENT AND TRADEMARK OFFICE
CERTIFICATE OF CORRECTION

PATENT NO. : 6,818,682 B2
DATED : November 16, 2004
INVENTOR(S) : Falsafi et al.

It is certified that error appears in the above-identified patent and that said Letters Patent is hereby corrected as shown below:

<u>Title page,</u>
Insert Item -- [73] Assignee: 3M Innovative Properties Company, St. Paul, Minnesota USA --.

Signed and Sealed this

Twenty-second Day of November, 2005

JON W. DUDAS
*Director of the United States Patent and Trademark Office*